United States Patent [19]

Luebke et al.

[11] 4,372,980

[45] Feb. 8, 1983

[54] METHOD OF OPERATING A PRESSURE FRYER

[75] Inventors: Clement J. Luebke, Beloit, Wis.; John A. Mitchell; Lowell W. Daniels, both of Rockford, Ill.

[73] Assignee: Alco Standard Corporation, Valley Forge, Pa.

[21] Appl. No.: 269,550

[22] Filed: Jun. 3, 1981

Related U.S. Application Data

[62] Division of Ser. No. 68,108, Aug. 20, 1979, Pat. No. 4,296,310.

[51] Int. Cl.³ .................... G01N 33/02; G01N 33/28
[52] U.S. Cl. .......................... 426/231; 73/73; 99/337; 426/438
[58] Field of Search .............................. 426/231, 438; 23/230 HC; 340/631, 602, 604; 99/331, 337; 73/73, 75; 324/443, 65

[56] References Cited

U.S. PATENT DOCUMENTS

| 2,552,088 | 5/1951 | Davis | 340/631 |
| 2,716,165 | 8/1955 | Pfitzner | 340/631 |
| 3,821,925 | 7/1974 | Moore | 99/337 |

Primary Examiner—Raymond N. Jones
Assistant Examiner—George C. Yeung
Attorney, Agent, or Firm—Leydig, Voit, Osann, Mayer & Holt, Ltd.

[57] ABSTRACT

A pressure fryer having a vessel adapted to cook a food product within a bath of cooking oil. Means are provided for detecting the presence of water in the vessel and the bath and for automatically disabling the heater of the fryer if water is present in such quantity as to create a potentially unsafe condition.

1 Claim, 5 Drawing Figures

METHOD OF OPERATING A PRESSURE FRYER

This is a division of application Ser. No. 68,108 filed Aug. 20, 1979 now U.S. Pat. No. 4,296,310.

BACKGROUND OF THE INVENTION

This invention relates generally to a cooking device and more particularly to a pressure fryer of the type having a pressure-tight cooking vessel which is adapted to hold a bath of cooking oil and a food product such as chicken. The vessel of such a fryer may be heated either electrically or by a gas burner and is equipped with a removable cover which is adapted to be sealed to the vessel to establish a pressure-tight condition therein.

The fryer is operated by placing a quantity of cooking oil in the vessel, by activating the heater to raise the temperature of the oil, by placing the food product in the vessel and by then sealing the vessel with the cover. Pressure is generated in the vessel as the moisture in the product reaches the boiling point and vaporizes into steam. The pressure which is generated reduces the cooking time and also raises the boiling point of the juices in the product so that flavor is sealed in and less shrinkage occurs.

A dangerous condition may be created if the fryer is operated with the cover sealed and with a substantial quantity of water in the vessel. Water may be introduced into the vessel in a number of ways. For example, water from a frozen food product may accumulate in the oil in substantial quantities if the same oil is used repetitively for cooking several batches of product. A careless operator may attempt to heat water in the vessel in spite of instructions to the contrary. Also, water may be carelessly or accidentally left in the vessel after the latter has been cleaned. When the fryer is next used, oil may be unknowingly poured into the vessel on top of the water. When the fryer then is heated, some of the water may not vaporize because of the pressure within the vessel. But, when the pressure is released by removal of the cover, such water may quickly flash to steam and may cause hot oil to explode from the vessel and seriously burn the person who is operating the fryer.

SUMMARY OF THE INVENTION

The general aim of the present invention is to provide a new and improved cooking device which eliminates the danger of personal injury resulting from operation of the cooking device while water is present in the vessel.

A further object is to provide a cooking device which is incapable of being heated if more than a predetermined quantity of water is present in the vessel.

A more detailed object is to achieve the foregoing by detecting the presence of water in the vessel and by automatically disabling the heater of the cooking device if the quantity of water exceeds a safe value.

Still another object is to make advantageous use of the difference between the electrical resistance values of water and oil in order to detect if an unsafe quantity of water is present in the vessel.

The invention also resides in the novel use of the vessel as an electrode which coacts with a second electrode to form a relatively simple and inexpensive water detecting device.

These and other objects and advantages of the invention will become more apparent from the following detailed description when taken in conjunction with the accompanying drawings.

DETAILED DESCRIPTION OF THE PREFERRED EMBODIMENT

Figure 1:
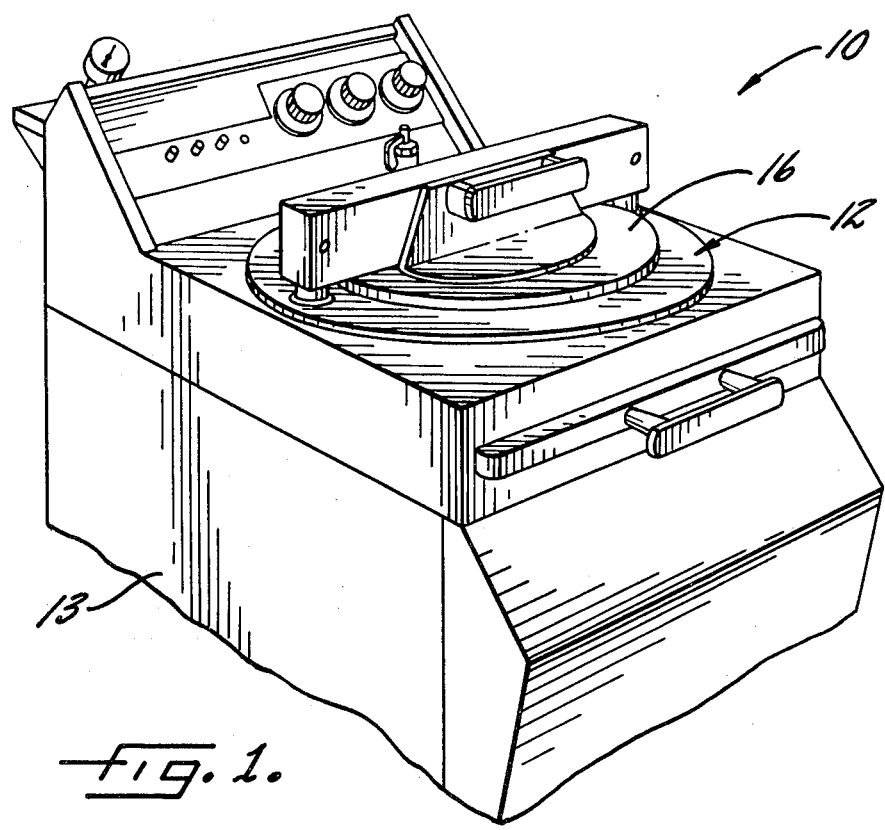
FIG. 1 is a fragmentary perspective view of a new and improved pressure fryer incorporating the unique features of the present invention.

As shown in the drawings for purposes of illustration, the invention is embodied in a cooking device which preferably is in the form of a pressure fryer 10 adapted to be used for cooking chicken, fish, potatoes and other food products under pressure and in a bath 11 (FIG. 3) of hot cooking oil. For the most part, the fryer is of conventional construction and thus the fryer itself has been shown and will be described only in sufficient detail to gain an understanding of the present invention.

Figure 2:
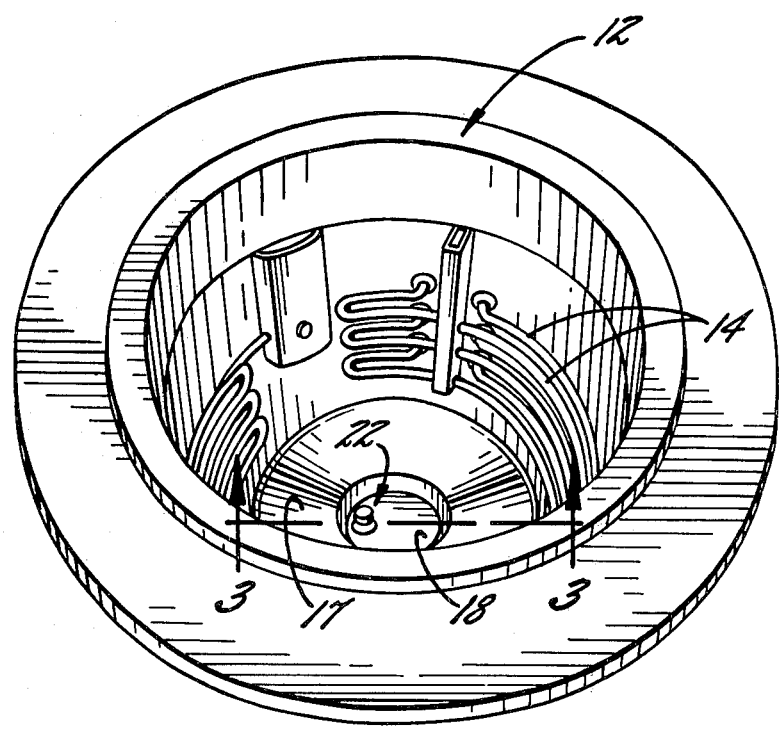
FIG. 2 is a perspective view looking into the vessel of the fryer.
Figure 4:
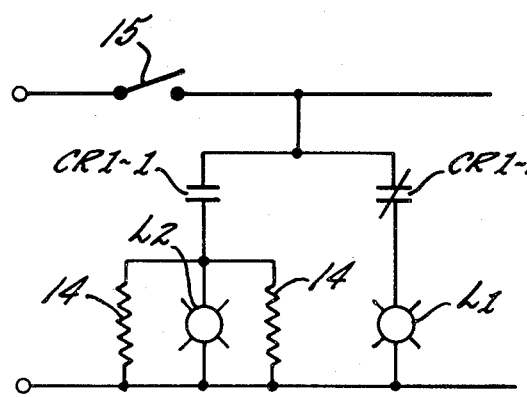
FIGS. 4 and 5 are diagrams of control circuits for the fryer.

In general, the fryer 10 comprises an open top vessel 12 supported by a cabinet 13 and defining a cooking well. Disposed within the lower portion of the vessel is an array of ring-like electrical resistance heating elements 14 (FIG. 2) adapted to be energized from an a.c. voltage source when a main control switch 15 (FIG. 4) is closed. Alternatively, the vessel may be heated by a gas-fired burner located outside of the vessel.

The vessel 12 is adapted to be sealed in a pressure-tight condition by a removable cover 16 (FIG. 1) which may be locked releasably to the top of the vessel. The vessel is generally cylindrical in shape except for a frusto-conical section 17 (FIG. 3) located beneath the heating elements 14, there being a reduced diameter well 18 located beneath the frusto-conical section.

To use the fryer 10, the vessel 12 is filled with a suitable cooking oil and then the heating elements 14 are energized to raise the oil to a predetermined temperature. Alternatively, solid shortening may be placed in the vessel and may be melted and heated to the required temperature by the heating elements.

After the oil has been heated, the chicken or other food product is placed in a wire mesh basket (not shown) which then is inserted into the vessel 12 and immersed in the oil. The bottom of the basket usually is located near the upper end of the frusto-conical section 17. Any breading, crumbs or the like which may fall off of the food slides down the frusto-conical section and is collected in the well 18.

After the food product has been placed in the vessel 12, the cover 16 is placed on the top of the vessel and is locked closed. During the cooking process, the moisture in the food product vaporizes and creates pressure in the vessel. Such pressure shortens the cooking time and also enhances the quality of the cooked product. A pressure relief valve (not shown) prevents the pressure within the vessel from exceeding about 12 p.s.i.

When the product has cooked for a predetermined period of time, the heating elements 14 are de-energized and the pressure within the vessel 12 is released. After the pressure drops, the cover 16 may be unlocked and removed to enable removal of the product. The product most desirably is removed as soon as possible after the pressure is released in order to reduce the absorption of oil by the product.

A potentially dangerous situation is created if any substantial quantity of water is present in the vessel 12 when the latter is closed and heated. Some water escapes into the cooking oil from the food product and particularly if the food product is initially frozen. If the oil is not changed with regularity, such water can accumulate to an unsafe quantity. Also, carelessness in attending to the fryer 10 can lead to the presence of water in the vessel. By way of example, the operating personnel may attempt to boil water in the vessel with the cover 16 closed even though operating instructions which accompany the fryer explicty warn against such use of the fryer. Also, water may be left in the vessel following cleaning of the vessel.

To explain the unsafe condition which might be created by the presence of water in the vessel 12, let it be assumed that the vessel has been cleaned and that some quantity of water has been left in the lower well 18. Let it further be assumed that the operator of the fryer has not noticed the water and has proceeded to fill the vessel with oil. Being lighter than the water, the oil will rest on the water and thus the water will tend to remain in the lower well 18.

When the vessel 12 is heated with the cover 16 closed, some of the water in the well 18 may not vaporize. This results because the well is located beneath the heating elements 14 and thus the water is not heated to as high a temperature as the oil. Also, the pressure in the vessel raises the boiling point of the water and may prevent the water from vaporizing. Accordingly, the water may remain in liquid form in the well 18 during the cooking process.

When the cooking operation is complete, the pressure within the vessel 12 is exhausted nearly to atmospheric pressure and then the cover 16 is removed. By virtue of the lower pressure and the hot oil being present in the vessel, the unvaporized water may quickly flash to steam and may cause the hot oil to gush rapidly out of the top of the vessel and burn the operator.

In accordance with the present invention, the fryer 10 is uniquely equipped with means 20 (FIG. 5) for detecting the presence of water in the vessel 12. If more than a predetermined quantity of water is present in the vessel or the oil bath 11, the detecting means automatically disable the heating elements 14 so as to prevent the vessel from being heated. In this way, the fryer cannot be operated at all if more than a predetermined quantity of water is initially present in the vessel. If water is extracted from the food product and accumulates to a predetermined quantity during operation of the fryer, the fryer will be shut down automatically to prevent the water from flashing to steam when the cover 16 is opened.

More specifically, the detecting means 20 herein comprise a pair of spaced electrodes 21 and 22 (FIGS. 4 and 5) adapted to be disposed in contact with the liquid bath 11 in the vessel and adapted to be conductively bridged by such bath. As is well known, the electrical resistance value of oil is much higher than that of water. Accordingly, when substantially pure oil is present in the bath, the resistance between the electrodes 21 and 22 is comparatively high and relatively little current may be conducted between the electrodes. If, however, water is present in the vessel or if the oil is contaminated with water, the electrical resistance of the liquid between the electrodes will be lower so as to allow current of higher magnitude to be conducted between the electrodes. When the resistance of the liquid between the electrodes drops below a predetermined threshold, a signal is produced and is used to de-energize the heating elements 14.

Figure 3:
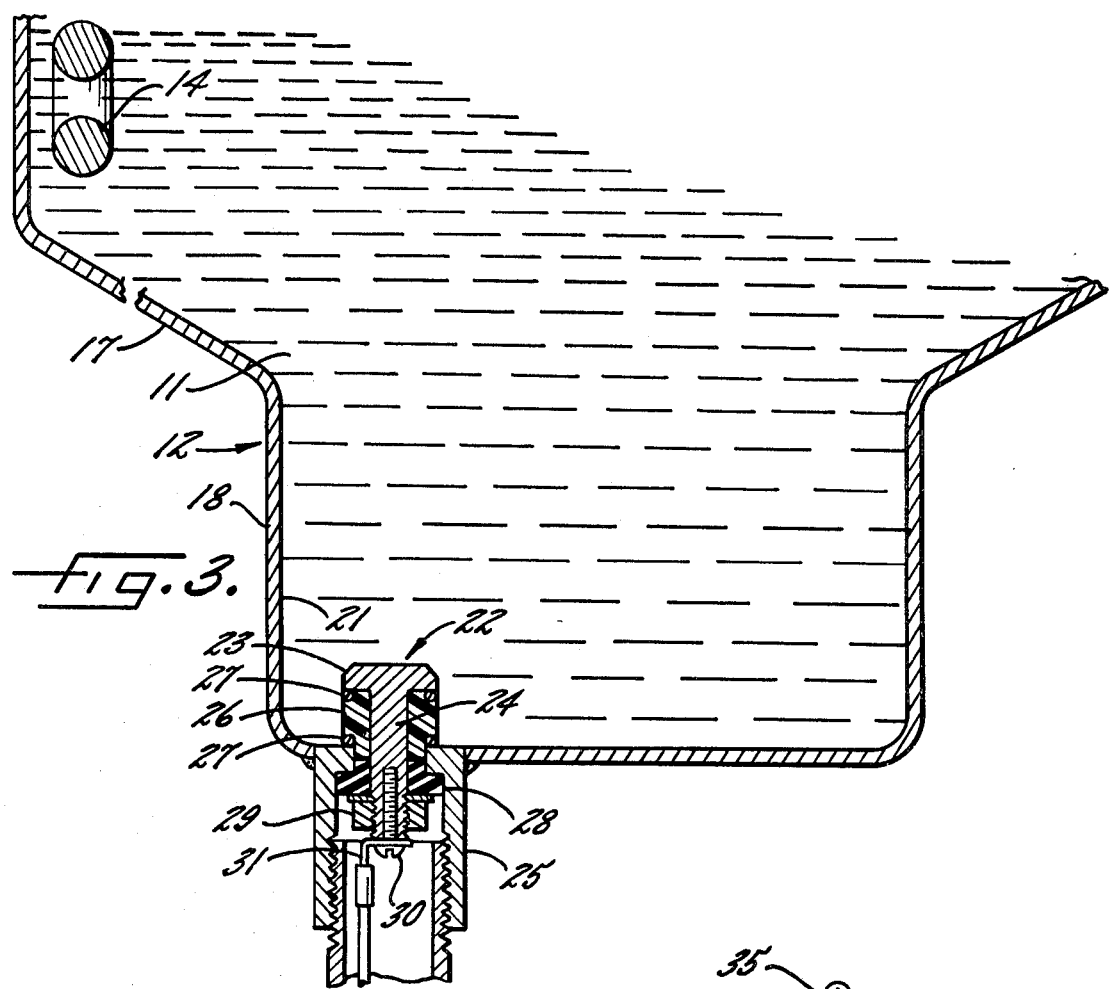
FIG. 3 is an enlarged fragmentary cross-section taken substantially along the line 3—3 of FIG. 2.

In carrying out the invention, the vessel 12 is made of electrically conductive metal, and the electrode 21 is advantageously formed by part of the vessel itself, for example, by one side wall of the lower portion of the well 18. The other electrode 22 is defined by the head 23 of a steel screw 24 (FIG. 3). The screw projects into the bottom of the vessel 12 and is located with its head 23 spaced a predetermined distance from the side wall 21 of the well 18.

As shown in FIG. 3, the screw 24 is supported by a tubular steel collar 25 which is welded into a hole in the bottom of the vessel 12. A Teflon bushing 26 and a pair of O-rings 27 are captivated between the upper end of the collar and the head of the screw in order to seal the vessel and to electrically insulate the upper end portion of the screw from the vessel. The lower end portion of the screw 24 is electrically insulated from the collar 25 by a nonconductive bushing 28 which is telescoped over the screw and which is held thereon by a nut 29. A threaded hole is formed in the shank of the screw 24 and receives a small screw 30 which serves to attach an electrical terminal 31 to the screw 24.

Figure 5:
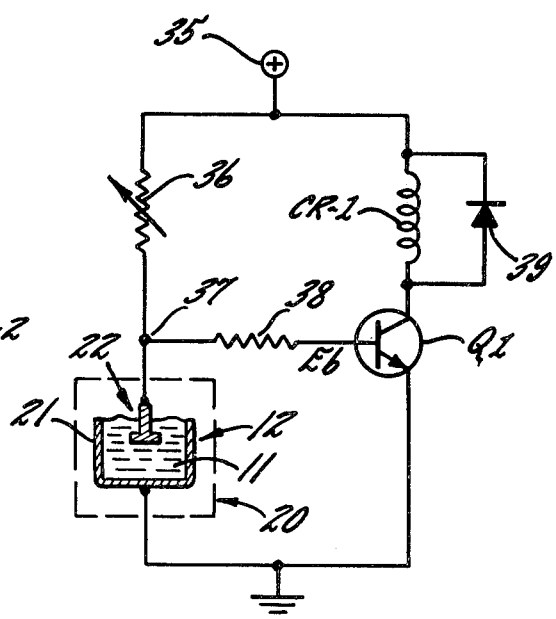

The terminal 31 of the electrode 22 is connected to the positive terminal of a suitable d.c. voltage source 35 (e.g., 6 volts d.c.) which is shown in FIG. 5 and which may be obtained by stepping down and rectifying the main a.c. voltage source of the fryer 10. The other electrode which is defined by the side wall 21 of the vessel 12 is, in keeping with the invention, common with the ground of the voltage source 35.

As shown in FIG. 5, a selectively adjustable resistor 36 (e.g., a rheostat) is connected in series with the voltage source 35 and the detecting means 20. The adjustable resistor 36 and the detecting means 20 form a voltage divider whose junction 37 is connected by way of a resistor 38 to the base of a grounded-emitter NPN transistor Q-1. A relay coil CR1 is connected in series with the voltage source 35 and the collector of the transistor while a flyback diode 39 is connected across the relay coil to absorb the inductive kick when the coil is de-energized. The coil CR1 controls a set of normally open relay contacts CR1-1 which are connected in series with the heating elements 14 and further controls a set of normally closed relay contacts CR1-2 which are in series with a warning light L-1. A second light L-2 is connected in parallel with the heating elements and is adapted to be lit whenever the heating elements are energized.

When the main control switch 15 is closed, the voltage at the junction 37 resides at a value which is determined by the setting of the adjustable resistor 36 and by the resistance of the liquid bath 11 between the electrode 22 and the other electrode defined by the side wall 21 of the vessel 12. If the bath consists of substantially pure cooking oil, the resistance of the liquid is relatively high and thus the voltage $E_b$ applied to the base of the transistor Q-1 is high so as to bias the transistor to "full on" and allow high collector-emitter current to flow from the voltage source 35 through the relay coil CR1. Such current energizes the coil to close the relay contacts CR1-1 so as to activate the heating elements 14 while turning on the power lamp L-2. At the same time, the relay contacts CR1-2 are opened to disable the warning lamp L-1. With the heating elements energized, the fryer 10 may be operated in a normal manner.

If water is present in the bath, the lower resistivity value of such water will lower the resistance between the electrode 22 and the side wall 21 of the vessel 12 so as to lower the value of the voltage $E_b$ applied to the base of the transistor Q-1. When the resistance of the liquid drops below a predetermined threshold, the voltage $E_b$ falls below a predetermined value and cuts off the transistor Q-1 so that current of high magnitude no longer is conducted through the collector-emitter path of the transistor. As a result, the relay coil CR1 is de-energized and opens its contacts CR1-1 to disable the heating elements 14. Accordingly, the bath will not be heated and thus there is no danger of the water vaporizing and causing the oil to gush from the vessel 12. When the relay contacts CR1-1 open to disable the heating elements, the power lamp L-2 is turned off and, at the same time, the relay coil CR1 closes the relay contacts CR1-2 to energize the lamp L-1 and warn the operator that oil is in the vessel.

By adjusting the resistance value of the resistor 36, the voltage $E_b$ which exists at the junction 37 can be adjusted for a given value of the resistance of the bath 11. In this way, the sensitivity of the detecting circuit can be decreased or increased to cause the heating elements 14 to be disabled when the quantity of water within the oil is at a higher or lower concentration. In other words, the adjustable resistor 26 enables the circuit to be calibrated so that the heating elements 14 will be disabled only when the concentration of water reaches what is determined to be an unsafe value. Thus, the fryer 10 may continue to operate if only small quantities of water are present in the oil.

From the foregoing, it will be apparent that the present invention brings to the art a new and improved pressure fryer 10 which eliminates the danger of operator injury caused by the existence of water in the vessel 12. If a substantial quantity of water is left in the vessel as a result of a cleaning operation, the detecting means 20 will sense the water and disable the heating elements 14 so as to make it impossible to even begin operation of the fryer until the water is removed. If water extracted from the food product during a cooking operation causes the water concentration to approach an unsafe level, the heating elements will be disabled automatically during the cycle and will prevent operation of the fryer until new oil has been placed in the vessel.

While the invention has been specifically disclosed in connection with the electric fryer 10, those familiar with the art will appreciate that the principles of the invention are applicable to a fryer having a gas-fired burner. In such an instance, relay contacts similar to the relay contacts CR1-1 control the solenoid for the main gas valve of the burner. When opened in response to the detection of a high quantity of water, the contacts de-energize the solenoid to shut the valve and disable the burner.

We claim:

1. A method of operating a pressure fryer having a vessel holding a food product and a bath of cooking oil, means for heating said bath, a removable cover for establishing a pressure-tight condition in said vessel when said bath is heated means in the lower portion of said vessel for detecting the presence of water in the lower portion of said vessel and for producing an electrical signal when more than a predetermined quantity of water is present in said vessel, and means in said circuit for automatically disabling said heating means when said signal is produced, said method comprising the steps of, manually actuating a main control to activate said heating means, detecting the presence of water in the lower portion of said bath, producing a signal when the concentration of water in the lower portion of said bath exceeds a predetermined threshold, and utilizing said signal to de-activate said heating means independently of said main control and independently of any manual operation thereby to prevent operation of the heating means when the concentration of water in the lower portion of said bath is in excess of said predetermined threshold, whereby said concentration of water is prevented from flashing into steam which causes the hot cooking oil to gush rapidly out of the top of the vessel when the cover is removed.

* * * * *